United States Patent [19]

Luceyk

[11] 4,126,558

[45] Nov. 21, 1978

[54] BLOOD FILTRATION UNIT WITH MANUAL VENT MEANS

[75] Inventor: Alfred R. Luceyk, Santa Paula, Calif.

[73] Assignees: Johnson & Johnson, New Brunswick, N.J.; Purolator, Inc., Del.

[21] Appl. No.: 743,449

[22] Filed: Nov. 22, 1976

Related U.S. Application Data

[60] Continuation-in-part of Ser. No. 545,961, Jan. 31, 1975, abandoned, which is a division of Ser. No. 473,479, May 28, 1974, Pat. No. 3,954,623.

[51] Int. Cl.² .................. B01D 21/24; B01D 23/20; B01D 25/30; B01D 29/42
[52] U.S. Cl. ........................................ 210/429; 55/310; 128/214 R; 137/549; 137/DIG. 4; 210/436; 210/472; 210/DIG. 23; 251/321

[58] Field of Search ................. 210/90, 120, 131, 132, 210/436, 437, DIG. 23, 472, 92, 430, 431, 432, 429; 55/385 C, 310, 311; 137/DIG. 4, 549; 251/321; 128/214 C, 214 R, 214.2; 222/518, 189, 3, 2, 380, 387, 402.1, 442

[56] References Cited

U.S. PATENT DOCUMENTS

| | | | |
|---|---|---|---|
| 1,676,034 | 7/1928 | Langdon | 222/518 |
| 1,687,120 | 10/1928 | Blanchard | 222/518 |
| 2,447,142 | 8/1948 | Smith et al. | 222/189 |
| 2,707,562 | 5/1955 | Kasten | 210/436 |
| 3,192,949 | 7/1965 | De See | 137/DIG. 4 |
| 3,316,908 | 5/1967 | Burke | 222/189 |
| 3,567,130 | 3/1971 | Holt | 222/189 |
| 3,701,433 | 10/1972 | Krakauer | 210/DIG. 23 |
| 3,881,640 | 5/1975 | Noble | 128/214 C |
| 3,901,808 | 8/1975 | Bokros | 210/DIG. 23 |
| 3,970,219 | 7/1976 | Spitzer et al. | 222/189 |

Primary Examiner—Tim R. Miles
Assistant Examiner—Frank Sever

[57] ABSTRACT

The improvement in a blood filtration unit for filtering multiple units of blood comprising means for filtering air entering the unit.

2 Claims, 5 Drawing Figures

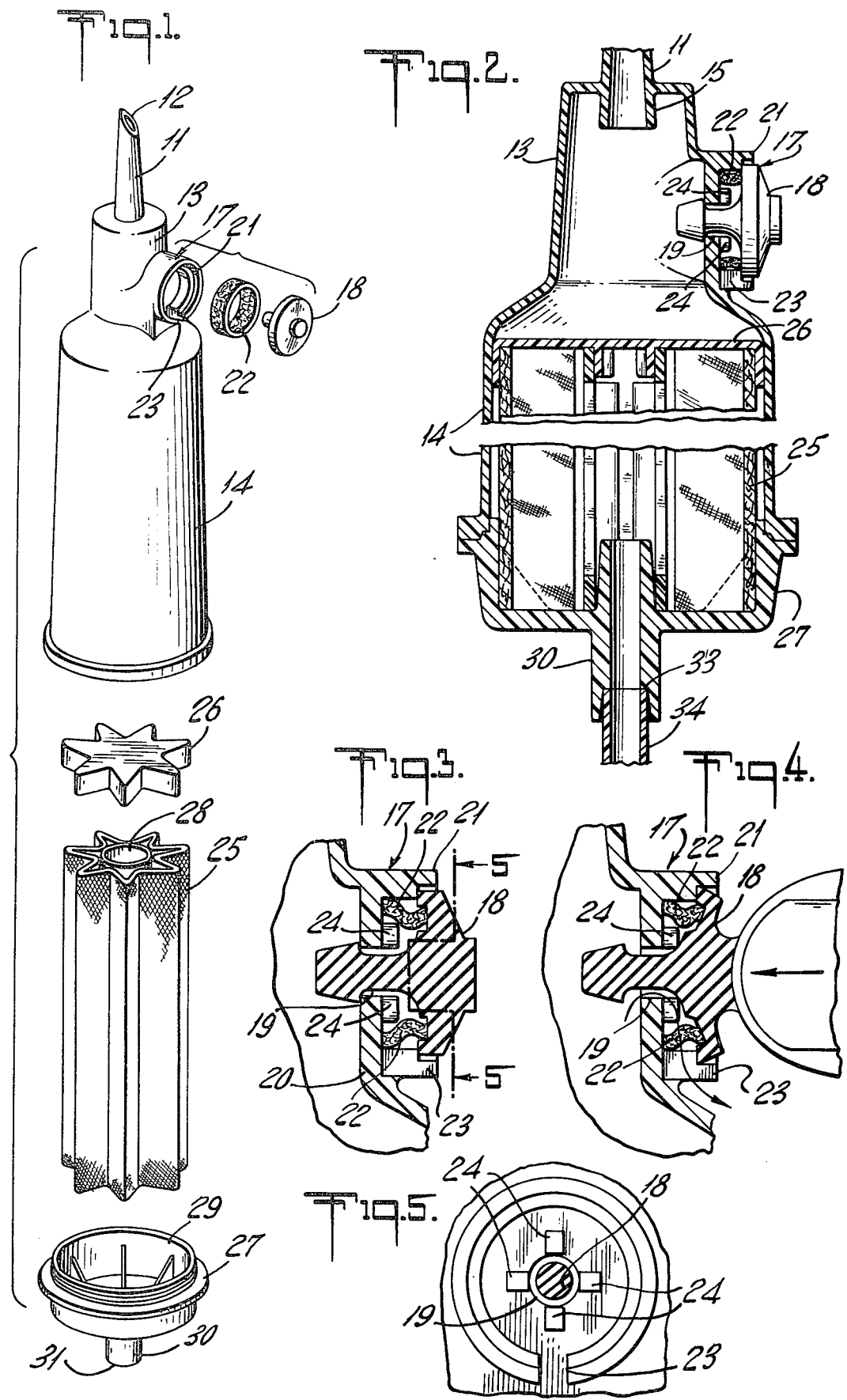

BLOOD FILTRATION UNIT WITH MANUAL VENT MEANS

This is a continuation-in-part Application of copending application Ser. No. 545,961, filed Jan. 31, 1975, now abandoned, which was a division of application Ser. No. 473,479, filed May 28, 1974 now U.S. Pat. No. 3,954,623.

BACKGROUND OF THE INVENTION

In the administration of whole blood to a patient it is desirable, if not necessary, to filter the blood as it is being administered. The debris which is to be removed by the filter will vary depending upon the length of time the blood has been stored. Over the years, many different filter media have been developed which are specifically useful in filtering debris from whole blood. Although the engineering of the filter media and the filter efficiency is extremely important there are a number of other problems involved with filtering blood during blood transfusions. First, in administering blood to the patient and in filtering this blood, the flow rate should be known and controlled. The filtration unit should be readily insertable into a blood reservoir, usually a blood bag, and the necessary administration sets for administering blood to the patient easily and readily connected to the filtration unit in a manner that does not disrupt or change the flow of the blood. The filtration unit should be constructed so not to collect or entrap micro-gas bubbles which might be administered inadvertently to the patient. The unit itself should have a low total volume so that blood is not held in the unit and all of the blood from a blood bag is administered to the patient. The filtration unit should be easily and readily primed and primed in such a manner as not to entrap gas bubbles. Along with all of these problems which should be overcome, the unit should have excellent filtering efficiency, do as little damage to the blood components as possible, and be usable for multiple blood transfusions to a single patient in order to be reasonably economical.

SUMMARY OF THE PRESENT INVENTION

We have discovered a new and improved blood filtration unit. The flow of blood through our unit is measurable and known. The efficient manner in which the filter media is used in our unit is improved, and the possible blockage of the media is reduced. Our new filter unit does little, if any, damage to the blood components being filtered. In certain embodiments of out new filter unit, it may be readily and easily primed or filled without entrapping gas bubbles and filtered blood may be drained from the unit so there is very little blood held-up or retained in the unit and substantially all the blood is available to the patient. In other embodiments of our new filtration unit administration sets are easily insertable into the filtered blood outlet in a manner that insures a uniform flow rate and reduces the possibility of entrapment of micro-gas bubbles by the filtered blood stream. Our blood filtration unit may be used for multiple administration of units of blood and is economical.

In accordance with the present invention, our new blood filtration unit comprises a filter cartridge disposed within a filter housing. Attached to the top of the filter housing is a drip chamber for measuring blood flow. Attached to the top of the drip chamber is the blood inlet which extends into the chamber at its one end and is diagonally cut at its opposite end for easy insertion into a blood reservoir such as a bag of blood. The filter cartridge comprises filter media, a top end cap for sealing one end of the media and a bottom end member to seal the opposite end of the media but leave a hollow center core of the media open and directly connectable to the blood outlet. The bottom end member attaches to the housing to form the completed filtration assembly. The top cap is multipointed or star-shaped and has a diameter measured at the end of the points substantially the same or slightly smaller than the inside diameter of the housing. The filter cartridge is elongated and has a hollow center core. Its cross-sectional shape is substantially the same as the multipointed shape of the top end cap. The bottom member seals the bottom of the filter media and closes the housing. There is a centrally located outlet in the bottom member which connects directly to the center core of the media and to which an administration set may be connected. In use, blood flows from the blood bag to the drip chamber, down through the openings created by the multi-pointed filter cartridge into the segmented filtration compartments, through the media into the hollow center core and out through the blood outlet in the bottom end cap. In certain embodiments of our new blood filtration unit, a filtered air vent valve is placed in the side wall of the drip chamber so the unit may be readily primed and filled and entrapped gas evacuated. When the blood bag is emptied, the valve may be opened and the filtration unit drained to allow administration of substantially all of the filtered blood. When the vent valve is opened, the incoming air is filtered.

In certain embodiments of the blood filtration unit of the present invention, the blood outlet has a shoulder on its inlet side. The inside diameter of the outlet measured at this shoulder is the same as the inside diameter of the tubing of the administration set to be used with the unit to administer blood to a patient. This construction reduces the possibility of microgas emboli being entrapped in the area where the blood outlet and the administration set meet. This construction also provides for a uniform and constant flow rate of blood to the patient.

BRIEF DESCRIPTION OF THE DRAWINGS

The invention will be further described in conjunction with the accompanying drawings wherein:

FIG. 1 is an exploded view in perspective showing the assembly of the various parts of the new blood filtration unit of the present invention, FIG. 2 is a cross-sectional view of a blood filtration unit according to the present invention, FIG. 3 is an enlarged, cross-sectional view of a filter air vent valve in accordance with the present invention with the valve in the closed position, FIG. 4 is an enlarged, cross-sectional view of the air vent valve shown in FIG. 3 with the valve in the open position, and FIG. 5 is a cross-sectional view taken along line 5—5 of FIG. 3.

The same numeral has been used for similar parts throughout the Figures.

DETAILED DESCRIPTION OF THE DRAWINGS

Referring to the drawings in FIG. 1, there is shown a blood filtration unit in accordance with the present invention. At the top of the unit is the blood inlet 11. One end 12 of the blood inlet is tapered or diagonally cut for easy insertion into a reservoir of blood such as the plastic blood bags commonly in use. The blood bag contains a weakened portion, circular in shape, and the tapered spike-like inlet is readily insertable into this weakened portion. The opposite end of the blood inlet extends into the drip chamber 13 which is at the top of the housing 14 for the unit. As may be more clearly seen in FIG. 2, the extension 15 into the drip chamber 13 allows blood to drip into the unit and the number of drops may be counted and metered as desired. The height of the drip chamber should be as small as possible to reduce the impact force of the blood droplets on the distribution surface and minimize the blood-air interface contact time in order to reduce blood trauma.

Disposed in the side wall of the drip chamber is an air vent valve 17. The valve is more clearly shown in FIGS. 3, 4 and 5. The valve comprises a resilient member 18 which extends through a hole 19 in the wall 20 of the drip chamber. As shown in the drawings, the resilient member has a circular portion which is positioned on the outside of the housing. Disposed from this circular portion is a reduced diameter portion that extends through the opening 19. This reduced diameter portion ends in an expanded portion disposed inside the housing and which expands outwardly to seal along the inside surface of the wall. The periphery of the circular portion of the resilient member on the outside of the housing contacts the outside surface of the housing. This contact may be accomplished by numerous designs. One such design is shown in the drawing wherein on the outside surface of the wall and around the entry hole is a circular ledge 21. The periphery of the circular portion of the resilient member contacts this ledge 21. An annular shaped filter media 22 is positioned within the circular ledge. The media contacts the wall surface on one side and the resilient member on the other side. The circular ledge carries an opening 23 to allow air to escape or enter through the valve. There, of course, could be an opening, to allow the escape of air, at the edge of the circular portion of the resilient member or other similar designs as desired. When the filtration unit is to be filled, the resilient member is pushed in as shown in FIG. 4, allowing air within the unit to escape out through the entry hole and the opening in the circular ledge. A number of stops 24 ar disposed about the entry hole to prevent sealing of the hole when pushing in the resilient member. When the unit is filled to a desired level with blood, the valve is released and automatically closes. To drain the unit, the valve is pressed inwardly to allow air to enter the blood filtration unit and allow the unit to drain. The air entering the unit is filtered through the annular filter media.

Disposed from the drip chamber is the portion of the housing that encloses the filter cartridge. The filter cartridge itself comprises filter media 25, a top end cap 26 and a bottom member 27. The top end cap is solid and multi-pointed or star-shaped. It is preferred that the end cap have from about four to ten points to produce between four and ten segmental filter compartment areas in the unit. The media is in the form of an elongated member having a hollow center core. Its cross-sectional shape is the same as the multi-point shape of the top end cap. If desired, a permeable center core 28 may be disposed in the media for structural purposes and such a core may be wrapped with a fine media to aid in the filtration as desired. One end of the media is sealed by the top end cap and the other end of the media is sealed into the bottom member. The outer periphery 29 of the bottom member 27 is attachable to the housing 14. The bottom member contains a centrally located outlet 30 which connects to the center core of the media at one end with the other end 31 adaptable to connect with various types of administration sets or administration set tubing.

In one embodiment of the present invention, the outlet is constructed as shown in FIG. 2. Within the blood outlet 30 there is small shoulder 33 which extends into the opening. The inside diameter of this shoulder is exactly the same as the inside diameter of the tubing 34 of the administration set to be used. The tubing is inserted in the downstream side of the outlet up against the shoulder. If desired, the tubing may be adhered or bonded to the inside surface of the outlet. Also, if desired, the outlet may be slightly tapered to aid in insertion. An advantage of this construction is that no air can be entrapped where the tubing and the blood outlet meet and this eliminates the possibility of entrapping small air bubbles during administration of the blood. This configuration also provides a uniform diameter from the filtration unit to the needle administering blood to the patient and a constant and uniform blood flow.

The housing for the filter unit may be made from any of the plastic materials which are inert and have no effect on blood. Examples of such materials are the polycarbonates, the butadienestyrenes and the like. Similar materials may be used for the top end cap and the bottom end member. generally, it is preferred to use clear materials for the housing.

The filter media which may be used with the unit are any of the various depth, semi-depth, or sieve type medias or various combinations of these medias. Suitable media are woven fabrics made from synthetic filaments, foam materials, nonwoven fabrics and the like. A preferred filter media for the transfusion of blood is a combination of a woven polyester fabric having a mean pore size opening of 160 to 180 microns as the first or upstream layer. The second or downstream layer is a needlepunched nonwoven fabric of polyester fibers weighing about nine ounces per square yard. The layers may be separated by an open plastic mesh material for support and stability. In some instances, a third or further downstream layer may be used such as a woven nylon fabric having a mean pore size rating of about 20 microns. This media is used to prevent lint or fibers which may sluff off or be removed from the nonwoven media from entering the bloodstream. If desired this media may be wrapped around a supporting core to act in the way described.

The air vent valve is made from resilient material which is inert to blood such as natural, synthetic or silicone rubber. The valve is resilient and readily deformable and provides a good seal with the material from which the housing is made. The air filter media used with the valve may be any of the standard air filtration materials such as a needlepunched polyester or other synthetic fiber batts and the like.

In our new filtration unit, the design is important in order to reduce the holding capacity of the unit itself while providing good flow characteristics for the filtration of blood. The drip chamber is as small a diameter as possible and is flared out to the filter cartridge to provide good flow characteristics. During use, it is preferred that the blood level be maintained above the top cap of the filter cartridge so that blood drops hit a liquid surface rather than a solid surface to reduce the possibility of blood damage. The filter cartridge is star-shaped to provide a large filtration area and good filtration efficiency while also maintaining the volume as low as possible. As previously mentioned, from about four to ten points may be used to provide the necessary area of filtration. The points of the star are substantially in contact with the inside surface of the housing. This configuration produces the same number of filtration compartments as there are points on the end cap. The blood from the filter bag can flow into all of the filtration compartments. Should the filter media in one of these compartments start to become blocked, the remaining compartments are still available for filtration and provide for efficient filtration, even as the media may become blocked.

Having now described out new blood filtration unit, it will become apparent to those skilled in the art of the many variations and changes that may be made without departing from the spirit and scope of the present invention. All we desire to be limited to is that described in the appended claims.

What is claimed is:

1. In a blood transfusion filtration unit having a filter cartridge disposed within a housing the improvement comprising a manually operable air vent valve disposed in the upper portion of said housing said air vent valve comprising an actuating member, said member comprising a circular portion disposed on the outside of said housing, said circular portion having a resilient periphery in contact with the outside surface of said housing, a reduced diameter portion extending from the center of said circular portion through an opening in the housing and an expanded and portion disposed from said reduced diameter portion within the housing; and end portion functioning to provide a seal with the inside surface of said housing; an annular air filtration media disposed between the housing and the resilient periphery of said circular portion of said actuating member on the outside of the housing; said resilient periphery being deformed in response to manual pressure applied to said circular portion so as to bias said expanded end portion in such a manner as to break said seal and provide a continuous unobstructed flow path for air from within said housing, through said filtration media, to atmosphere.

2. A blood transfusion filtration unit in accordance with claim 1 wherein the housing incorporates a circular ledge extending outwardly from said housing, the resilient periphery of the circular portion of the actuating member contacts said ledge and said ledge includes an opening for the passage of air.

* * * * *